United States Patent [19]

Sakamoto et al.

[11] 4,447,355

[45] May 8, 1984

[54] METHOD FOR STABILIZING A TUMOR NECROSIS FACTOR AND A STABLE AQUEOUS SOLUTION OR POWDER CONTAINING THE SAME

[75] Inventors: Hajimu Sakamoto; Takao Kiyota; Hiroshi Hayashi, all of Fuji, Japan

[73] Assignees: Asahi Kasei Kogyo Kabushiki Kaisha; Dainippon Pharmaceutical Co., Ltd., both of Osaka, Japan

[21] Appl. No.: 477,866

[22] Filed: Mar. 23, 1983

[30] Foreign Application Priority Data

Apr. 7, 1982 [JP] Japan .................................. 57-56690
Jul. 27, 1982 [JP] Japan .................................. 57-129560

[51] Int. Cl.$^3$ .............................................. C07G 7/00
[52] U.S. Cl. ........................... 260/112 B; 260/112 R; 260/117; 260/121; 424/101; 424/177
[58] Field of Search ............... 260/112 R, 112 B, 121, 260/117; 424/101, 177

[56] References Cited

PUBLICATIONS

Infec. Immun. 33(1), 156–164 (1981), Mannel et al.
Infec. Immun. 30(2), 523–530 (1980), Mannel et al.
Proc. Nat. Acad. Sci. USA, 72(9), 3666–3670(1975), Carswell et al.
Proc. Nat. Acad. Sci. USA, 73(2), 381–385 (1976), Green et al.
Expl. Cell Biol. 47 53–60 (1979), Helson et al.
Brit. J. Cancer 38, 302–309 (1978), Matthews et al.
Brit. J. Cancer 42, 416–422 (1980), Matthews et al.
Infect. Immun. 28(1), 204–211 (1980), Mannel et al.
Brit. J. Cancer, 44, 418–424, (1981), Matthews.
Infec. Immun. 33 (2), 527–530 (1981), Fernandes et al.
Infects. Immun. 30(1), 159–164 (1980) Anderson et al.
J. Natl. Cancer Inst. 59 (5), 1519–1522 (1977), Green et al.
Lymphokines, vol. 2, edited by E. Pick, 245–248 (1981).
Infect. Immun. 33(2), 523–526 (1981), Oseas et al.
J. Immunol. 126(4), 1279–1283 (1981), Kull et al.
Science, 130, 432–437 (1959), Eagle.

Primary Examiner—Howard E. Schain
Attorney, Agent, or Firm—Pennie & Edmonds

[57] ABSTRACT

A method for stabilizing a Tumor Necrosis Factor (TNF), which comprises adding at least one member selected from the group consisting of an albumin, a gelatin, a globulin, a protamine and a salt of protamine to an aqueous solution or powder containing TNF, and a stable aqueous solution or powder which contains TNF and an effective amount of such a protein. The aqueous solution or powder containing TNF can be stored for a prolonged period of time without losing its activity, and is stable on freezing, thawing, lyophilization or the like.

47 Claims, 4 Drawing Figures

METHOD FOR STABILIZING A TUMOR NECROSIS FACTOR AND A STABLE AQUEOUS SOLUTION OR POWDER CONTAINING THE SAME

This invention relates to a method for stabilizing a Tumor Necrosis Factor, and more particularly to a method for stabilizing a Tumor Necrosis Factor, in which a specific protein is added to an aqueous solution or powder containing a Tumor Necrosis Factor. This invention also relates to a stable aqueous solution or powder which contains a Tumor Necrosis Factor and an effective amount of such a specific protein.

Carswell et al discovered a Tumor Necrosis Factor (hereinafter simply referred to as "TNF"). They reported that TNF is a substance found in the serum of endotoxin-treated mice, rats or rabbits which had been sensitized with an immunopotentiator such as bacillus Calmette-Guérin (BCG), Corynebacteria or Zymosan, and that TNF induces necrosis in a variety of transplanted mouse tumors, with no toxic effect upon the tumor-bearing recipient [see Proc. Nat. Acad. Sci. USA, 72(9), 3666–3670(1975)].

Thereafter, numerous reports have been published with respect to the biochemical and physiological properties of mouse TNF and rabbit TNF [see, for example, Proc. Nat. Acad. Sci. USA, 73(2), 381–385(1976); Expl. Cell Biol., 47, 53–60 (1979); Br. J. Cancer, 38, 302–309(1978); and ibid., 42, 416–422(1980)]. It is noted that a cytotoxic factor, which is a substance suggested to be identical with TNF, has also been reported by some researchers [see, for example, Infect. Immun., 28(1), 204–211(1980)].

The production in vitro of TNF has also been reported. For example, Matthews determined and reported the optimal conditions under which TNF is produced in vitro by the mononuclear phagocytes from various tissues of normal and BCG-injected rabbits [see, Br. J. Cancer, 44, 418–424(1981)]. According to his report, the optimal amounts of TNF are produced by mononuclear phagocytes in the presence of endotoxin, and alveolar and peritoneal macrophages are the most potent producers of TNF. Further, according to his report, the macrophages from BCG-injected rabbits produce significantly more TNF than those from normal animals. Meanwhile, Männel et al reported that the macrophage-enriched peritoneal exudate cells from BCG-infected mice release a cytotoxic factor when stimulated in vitro with lipopolysaccharide (endotoxin) [see, Infect. Immun., 30(2), 523–530(1980); and ibid., 33(1), 156–164(1981)].

With respect to the characteristic properties of TNF, it is known that TNF, in addition to its activity of inducing necrosis in a variety of tumors, exerts an activity not specific to the species of creatures. For example, rabbit TNF can induce necrosis in mouse tumors. Further, it is known that TNF, in vitro, does not impose any significant cytotoxic effect on the normal cells and has a cytotoxic effect on certain kinds of neoplastic cell lines (for example, L-M and Meth-A cells). As stated above, TNF has an antitumor activity, exerts an activity not specific to the species of creatures and does not impose any significant harmful effect on the normal cells. Therefore, expectations for the clinical application of TNF as an antitumor medicine have been great in the art.

It is also known that only a very small amount of TNF is induced in a mammal or tissue culture system. Accordingly, in order to ensure the wide and safe clinical application of TNF as an antitumor medicine, it is absolutely necessary to isolate and highly purify the crude TNF induced in a mammal or tissue culture system. Further, when large-scale production of the TNF to be used as an antitumor medicine is performed, it is usually needed to store the highly purified TNF in the form of a solution or a frozen mass over a prolonged period of time and lyophilize the TNF solution. However, the present inventors have found that the activity of highly purified TNF markedly drops on storing, freezing, thawing and lyophilizing it.

As far as the present inventors are aware, there has been no report in which the stability of highly purified TNF is studied. Under these circumstances, the efficient and steady supply of highly purified TNF, especially on a commercial scale cannot be ensured, despite the knowledge that TNF is an effective antitumor medicine.

To overcome the above-elucidated difficulty with respect to the stability of TNF, the present inventors have made extensive and intensive studies. As a result, it has been found, quite surprisingly, that addition of an effective amount of a specific protein as a stabilizing agent to an aqueous solution or powder containing TNF enables the TNF to be stored over a prolonged period of time without losing its activity and renders the TNF stable on freezing, thawing, lyophilization or the like. Based on this novel finding, the present inventors have completed this invention.

It is, therefore, an object of the present invention to provide a method for stabilizing TNF.

It is another object of the present invention to provide a stable TNF solution or powder which maintains its activity over a prolonged period of time and which is stable on freezing, thawing, lyophilization or the like.

The foregoing and other objects, features and advantages of the present invention will be apparent to those skilled in the art from the following detailed description and appended claims taken in connection with the accompanying drawings in which:

Figure 1:
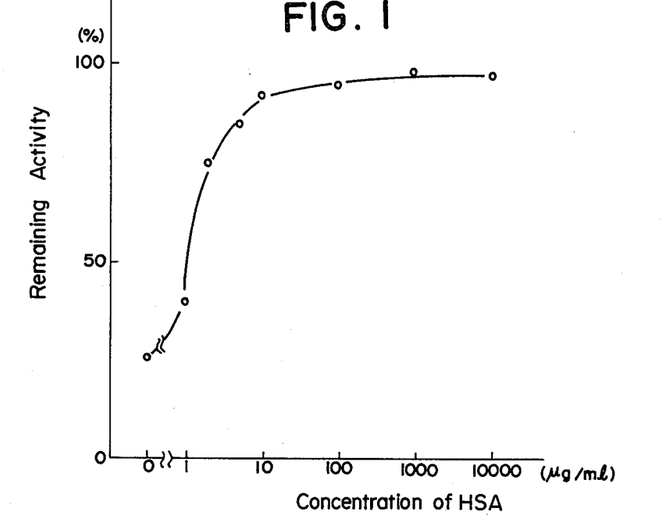
FIG. 1 is a graph showing the effect of the concentration of human serum albumin on the remaining activity of TNF after storage at 4° C. for 7 days.
Figure 2:
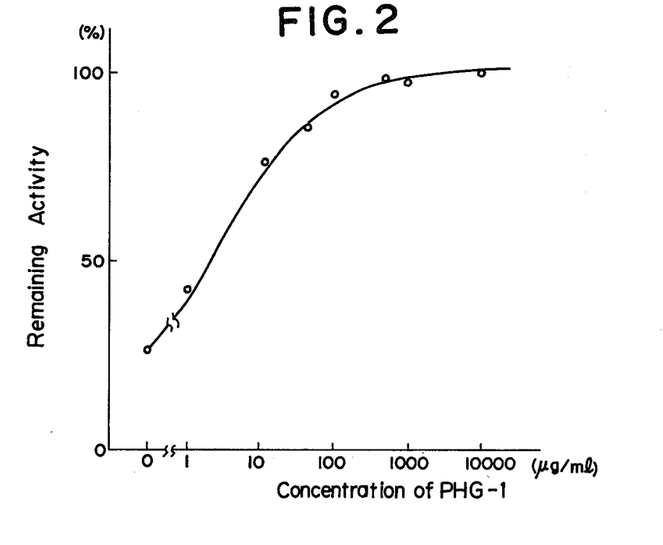
FIG. 2 is a graph showing the effect of the concentration of partially hydrolyzed gelatin on the remaining activity of TNF after storage at 4° C. for 7 days.
Figure 3:
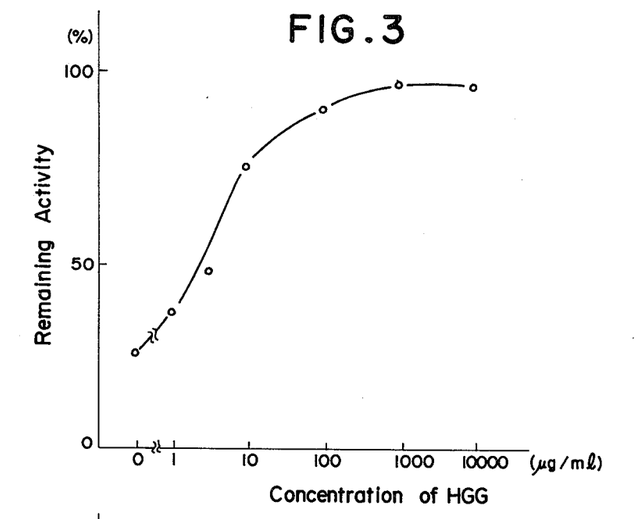
FIG. 3 is a graph showing the effect of the concentration of human gamma globulin on the remaining activity of TNF after storage at 4° C. for 7 days.
Figure 4:
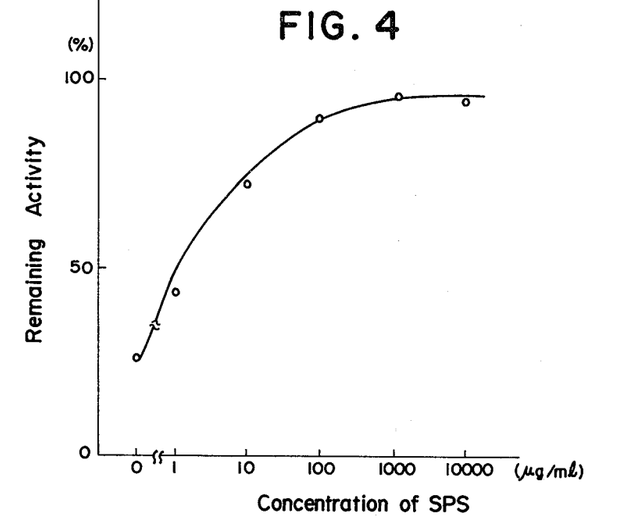
FIG. 4 is a graph showing the effect of the concentration of salmon protamine sulfate on the remaining activity of TNF after storage at 4° C. for 7 days.

A further detailed explanation of the Figures will be given later with respect to Example 2.

In one aspect of the present invention, there is provided a method for stabilizing TNF, which comprises adding to an aqueous solution or powder containing TNF an effective amount of at least one stabilizing agent selected from the group consisting of an albumin, a gelatin, a globulin, a protamine and a salt of protamine.

In another aspect of the present invention, there is provided a stable aqueous solution or powder which contains TNF and an effective amount of at least one stabilizing agent selected from the group consisting of an albumin, a gelatin, a globulin, a protamine and a salt of protamine.

The term "TNF" as used herein denotes a physiologically active substance that is induced by administering at least one substance having a capacity for stimulating the reticuloendothelial system to a mammal and then injecting endotoxin from a Gram-negative bacterium into the mammal, or by adding endotoxin from a Gram-negative bacterium to a tissue culture system containing activated macrophages from a mammal, which substance causes necrosis of some tumors when passively transferred to tumor-bearing mammals, or a substance produced by any method and having the properties similar to those of the above physiologically active substance.

TNF to be employed in the present invention is produced by a plurality of processes known in the art, including the process of Matthews et al [see Br. J. Cancer, 42, 416–422 (1980)] and the process of Green et al [see J. Natl. Cancer Inst., 59(5), 1519–1522(1977)].

Typical procedures for preparing TNF to be employed in the present invention are as follows. First, at least one substance having a capacity for stimulating the reticuloendothelial system is injected intravenously or intraperitoneally into a mammal (e.g. mouse, rabbit, guinea pig, etc.). As the substances having a capacity for stimulating the reticuloendothelial system, there are generally used Gram-positive bacteria, protozoas or yeasts, which are administered to the mammal in state of either of living microorganisms, dead microorganisms (e.g. after heat treatment or formalin treatment) and microorganism cells extract. Examples of the Gram-positive bacteria include Propionibacteria such as *Propionibacterium acnes (Corynebacterium parvum) and Propionibacterium granulosum (Corynebacterium granulosum)*, Mycobacteria such as bacillus Calmette-Guérin (BCG) and *Mycobacterium smegmatis*, and Nocardias such as *Nocardia erythropolis* and *Nocardia gardneri*. As a suitable protozoa, for example, Plasmodium or Toxoplasma is employable. As a suitable yeast, Zymosan extracted from *Saccharomyces cerevisiae* or others is generally used. There may also be employable synthetic high molecular compounds such as pyran copolymer. Second, 7 to 14 days after administration of the above-mentioned substance having a capacity for stimulating the reticuloendothelial system, endotoxin from a Gram-negative bacterium, for example, a lipopolysaccharide derived from *Escherichia coli, Pseudomonas aeruginosa,* or *Salmonella typhosa* is injected intravenously into said mammal. Third, 1.5 to 2 hours after the injection, body fluids (e.g. ascites, lymph, etc.) and/or serum or plasma of said mammal are taken or internal organs such as liver, spleen, etc. are homogenized and extracted with a physiological saline solution. These body fluids, serum, plasma and/or extract of internal organs may be employed as crude solution of TNF. Of them, however, serum or plasma is generally employed.

As mentioned above, the method for preparing TNF to be employed in the present invention is not limited to the above method. The method based on gene engineering and the tissue culture method in which cells having a TNF-producing capacity are employed can also be effectively utilized. It is to be noted that these methods are also applicable to production of human TNF as well.

The crude TNF produced by any of the methods as set forth above may be purified using the below-cited conventional biochemical techniques singly or in combination to give an aqueous purified TNF solution, which is lyophilized to give a purified TNF powder. As the suitable biochemical technique for purification of TNF, there can be mentioned, for example, a salting-out technique in which ammonium sulfate is employed, an ion exchange chromatography in which an anion exchange resin is employed, a gel filtration technique and an electrophoresis technique. As the purity of TNF is increased by practicing the above techniques for purification, it is recognized that the TNF gradually becomes instable. For example, a TNF sample so purified as to have a specific activity of 500,000 units/mg (the specific activity is expressed as units of TNF activity per mg of protein; the unit of TNF activity is defined later) is quite instable as seen from the data given in the Examples. Even the TNF samples having a specific activity lower than 500,000 units/mg also experience a decrease of the respective activity in some degree when they are in storage or subjected to freezing, thawing, lyophilization and other operations.

Accordingly, the present invention is directed to the stabilization of the TNF that has been purified to a high degree and has been rendered instable. The TNF to be stabilized according to the present invention may be either in the form of a solution or powder. However, it is preferred that the TNF to be stabilized be in the form of a solution.

It is preferred that the TNF solution to be stabilized according to the present invention constantly have a pH value of from 5 to 10, and, further, it is preferred that the solvent for the TNF solution to be stabilized be a suitable buffer. As the suitable buffer, there can be mentioned, for example, a phosphate buffer and a tris(hydroxymethyl)aminomethane-HCl buffer. According to need, a salt, such as sodium chloride and potassium chloride, is added to the TNF solution. For example, a salt is added to the TNF solution so as to prepare an isotonic solution, when the TNF solution is used for injection. The purpose of addition of a salt is not limited to the above. The concentration of such a salt in the TNF solution may be determined, depending on the purpose of addition of the salt. For example, when the ultimate TNF solution is used for injection, an isotonic solution is prepared from the TNF solution by addition of sodium chloride up to a concentration of 0.15M.

According to the method of the present invention, an effective amount of at least one stabilizing agent selected from the group consisting of an albumin, a gelatin, a globulin, a protamine and a salt of protamine is added to an aqueous solution or powder containing TNF.

As the suitable albumin, there can be mentioned albumins from various animals, such as bovine, horse, sheep, goat, chicken and human. As specific examples of the suitable albumin, there can be mentioned bovine serum albumin, human serum albumin, chicken egg albumin, bovine lactalbumin and human lactalbumin. No significant difference is observed, in respect of the ability to stabilize TNF, between the above-mentioned albumins. As the stabilizing agent for injection preparations, however, human serum albumin is most preferable.

As the suitable gelatin, there can be mentioned a regular gelatin produced by customary procedures and a partially hydrolyzed gelatin. The molecular weight of the gelatin is not critical. However, as the stabilizing agent for injection preparations, a water-soluble partially hydrolyzed gelatin is more preferable. The partially hydrolyzed gelatin is obtained by enzymatic hydrolysis of a gelatin by means of a proteolytic enzyme such as papain or by acid- or alkali-catalyzed hydrolysis of a gelatin.

As the suitable globulin, there can be mentioned serum globulins from various mammals, such as bovine, horse, sheep, goat and human, and derivatives thereof. No significant difference is observed, in respect of the ability to stabilize TNF, between the above-mentioned globulins. Of them, however, a gamma globulin and a derivative thereof obtained by enzymatic treatment or chemical modification of the starting globulin are more preferable. As the stabilizing agent for injection preparations, human gamma globulin and derivatives thereof, such as plasmin- or pepsin-treated human gamma globulin and sulfonated human gamma globulin, are most preferable.

As the suitable protamine, there can be mentioned protamines from suitable species of fish, such as salmon, herring and mackerel. As the suitable salt of protamine, there can be mentioned the hydrochloride, sulfate and phosphate of protamines. No significant difference is observed, in respect of the ability to stabilize TNF, between the above-mentioned protamines and salts thereof.

The stabilizing agents to be employed in the present invention may be used either alone or in mixture.

The stabilizing agent to be employed in the present invention is added in an amount of about 1 $\mu$g or more, preferably 10 $\mu$g or more, especially preferably 100 $\mu$g or more, per ml of the TNF solution having a TNF activity of $10^2$ to $10^9$ units/ml (the unit of activity is defined later). The upper limit of the amount of the stabilizing agent is usually determined from the viewpoints of the solubility of the stabilizing agent and viscosity of the resulting solution and from the economical viewpoint. The upper limit of the amount of the stabilizing agent is generally 50 mg, preferably 10 mg, per ml of the TNF solution. When the TNF to be stabilized is in a powdery form, the stabilizing agent is added in such an amount as will cause an aqueous solution, which is obtained by dissolving the powdery TNF to exhibit an activity of $10^2$ to $10^9$ units/ml, to have the above-mentioned concentrations of the stabilizing agent.

The way in which the stabilizing agent is added is not critical. For example, the stabilizing agent in a powdery form may be directly added to the TNF solution. Alternatively, the powder of the stabilizing agent may be dissolved, in advance, in water or a suitable buffer, and added to the TNF solution. Further, alternatively, the powder of the stabilizing agent may be mixed with the TNF powder. Addition of the stabilizing agent may be effected at any time during the purification step or the step of manufacturing pharmaceutical preparations.

When two or more different kinds of stabilizing agents are employed, they are added in such an amount that the total amount thereof falls within the amount range as defined above.

It is preferred that storing and purification of and manufacturing pharmaceutical preparations from the TNF solution in which a stabilizing agent to be employed according to the present invention is incorporated, if kept in the form of a solution, be performed at a temperature of from 0° to 30° C., more preferably from 0° to 10° C. When the TNF solution is stored in a frozen form, it is preferred that the temperature for storage be maintained below 0° C., more preferably below $-20°$ C.

The TNF solution in which an effective amount of at least one stabilizing agent, according to the present invention, is incorporated does maintain its TNF activity during the storing, whether it is in the form of a solution or in a frozen form, or during the steps of purification and manufacturing pharmaceutical preparations.

Further, the method for stabilizing TNF, according to the present invention, is also applicable to lyophilization. Illustratively stated, when TNF solutions (especially, in the case of highly purified TNF) are subjected to lyophilization, the activities thereof generally markedly drop. However, TNF solutions containing an effective amount of at least one stabilizing agent, according to the present invention, are lyophilized without losing its activity to give a TNF powder. The TNF powder may be dissolved to give a stable aqueous TNF solution in which the concentrations of the stabilizing agent and TNF fall within the range as defined above. The stabilizing agent as defined in the present invention may, alternatively, be incorporated in the lyophilized TNF preparations. When TNF is stored in a powdery form, it is preferred that the temperature for storage be maintained at 25° C. or below.

To assay the activity of TNF, there are usually employed two methods, i.e. the in vivo method in which the tumor necrosis effect is measured in vivo, and the in vitro method in which the cytotoxic effect on neoplastic cells is measured in vitro.

As the in vivo method, there can be mentioned, for example, the method of Carswell et al [see Proc. Nat. Acad. Sci. USA, 72(9), 3666–3670 (1975)]. According to this method, BALB/c sarcoma Meth A cells ($2 \times 10^5$ cells) are transplanted intradermally at armpit of each of (BALB/c$\times$C57BL/6)F$_1$ mice and, 7 days later, mice with tumors of 7–8 mm in diameter, good vascularization and no spontaneous central necrosis are selected for evaluation. A TNF sample (0.5 ml) diluted with a physiological saline solution is injected through the tail vein of each of the mice. The activity of the TNF sample is evaluated after 24 hours according to the following criterion.

($-$): no change ($+$): slight hemorrhagic necrosis ($++$): moderate hemorrhagic necrosis (central necrosis extending over approximately 50% of the tumor surface)

($+++$): marked hemorrhagic necrosis (massive necrosis leaving a small viable rim along the tumor periphery)

As the in vitro method for the assay of TNF activity, there can be mentioned, for example, the method of Ruff et al [see Lymphokines, Vol. 2, edited by E. Pick, Academic Press, N.Y., 245–248 (1981)] and the method of Kull et al [see J. Immunol., 126 (4), 1279–1283 (1981)].

The in vitro method that the present inventors have employed for the assay of TNF activity has been developed by improving the above-mentioned conventional methods. The in vitro method of the present inventors, in which the cytotoxic activity of TNF against L-M cells (American Type Culture Collection CCL 1.2) is measured, is carried out as follows. As culture vessels, there are employed 96-well microtiter plates produced by Flow Laboratories, Inc. (U.S.A.), and L-M cells are cultured in Eagle's minimum essential medium [see Science, 130, 432–437 (1959)] containing 10 v/v % heat-inactivated fetal calf serum. A TNF sample (0.1 ml) serially diluted with the medium and the L-M cell suspension (0.1 ml, $1 \times 10^4$ cells) are mixed in each well of the plates and the plates are incubated at 37° C. for 48 hours in an air containing 5% carbon dioxide. At the end of the culture period, a 20% aqueous solution of glutaraldehyde (20 μl) is added to fix the cells. After fixation, the plates are washed with distilled water and allowed to dry, and 0.05% methylene blue (0.1 ml) is added to stain the viable cells. The plates are thoroughly washed with distilled water to remove excess dye and allowed to dry. 3% Hydrochloric acid (0.2 ml) is added to each well to extract the dye from stained cells. Absorbance of each well at 665 nm is measured with Titertek Multiskan produced by Flow Laboratories, Inc. The absorbance is proportional to the number of viable cells. The TNF activity, unit(U)/ml, is defined as the reciprocal dilution of TNF that causes 50% cytotoxicity, and can be obtained by plotting the dilution versus the absorbance on a graph. All the TNF activities, assayed according to the in vitro method, as used hereinafter are expressed by the above-defined unit.

According to the method of the present invention, efficient and steady supply, on a commercial scale, of highly purified TNF, which is believed to be a clinically applicable effective antitumor medicine, can be ensured because in the method of the present invention, the activity of TNF is maintained during the storing, whether TNF is in the form of a solution a frozen mass or a lyophilized preparation, and during the steps of purification and manufacturing pharmaceutical preparations. It has also been found that the TNF solution or powder, in which at least one stabilizing agent selected from the group consisting of human serum albumin, a gelatin, human gamma globulin, a derivative of human gamma globulin, a protamine and a salt of protamine is incorporated, can be safely administered to the human body, wherefore the novel composition of the present invention is especially useful when TNF is clinically applied as an antitumor medicine.

The present invention will now be described in more detail with reference to the following Referential Example, Working Examples and Comparative Example that by no means limit the scope of the invention.

ABBREVIATIONS USED IN EXAMPLES

In the following Examples, the names of stabilizing agents are abbreviated as follows:
HSA: human serum albumin
BSA: bovine serum albumin
PHG-1: partially hydrolyzed gelatin obtained by alkali-catalyzed hydrolysis of gelatin (average molecular weight: about 7,000)
HGG: human gamma globulin
SPS: salmon protamine sulfate
HPS: herring protamine sulfate
BGG: bovine gamma globulin
CEA: chicken egg albumin
BLA: bovine α-lactalbumin
PHG-2: partially hydrolyzed gelatin obtained by acid-catalyzed hydrolysis of gelatin (average molecular weight: about 7,000)
PHG-3: partially hydrolyzed gelatin having a low gel strength
PG: purified gelatin
SPF: salmon protamine (free base)
SPP: salmon protamine phosphate
EDTA: ethylenediaminetetraacetic acid

REFERENTIAL EXAMPLE

Female rabbits, each weighing from 2 to 3 kg, were each injected intravenously with 75 mg of formalin-killed cells of *Propionibacterium acnes* (*Corynebacterium parvum;* Wellcome Research Laboratories, England). Eight days later, the rabbits were each injected intravenously with 100 μg of endotoxin (lipopolysaccharide from *Escherichia coli* 026:B6, produced by Difco Laboratories, U.S.A.). The blood was obtained from each rabbit by cardiac puncture 2 hours after the injection of endotoxin, and the blood obtained was mixed with a small amount of heparin. The blood was centrifuged at 3,000 rpm for 15 minutes. As a result, a plasma having a TNF activity of 2,500 U/ml was obtained.

The thus obtained plasma (10 liters) containing TNF was diluted with 5 liters of 0.03 M phosphate buffer (pH7.8). The diluted plasma was applied to a column (10×42 cm) of DEAE-Sepharose CL-6B (manufactured and sold by Pharmacia Fine Chemicals AB, Sweden) equilibrated with 0.03 M phosphate buffer (pH 7.8) containing 0.13 M NaCl. The column was washed with 2.5 liters of 0.03 M phosphate buffer (pH 7.8) containing 0.13 M NaCl, and the adsorbed TNF was eluted with a linear NaCl gradient consisting of 5.0 liters of 0.03 M phosphate buffer (pH 7.8) containing 0.15 M NaCl and 5.0 liters of 0.03 M phosphate buffer (pH 7.8) containing 0.3 M NaCl. The flow rate was 230 ml/hour and 45-ml fractions were collected. TNF activity was found in the fractions eluted with 0.20–0.24 M NaCl. The fractions with TNF activity were pooled and dialyzed overnight against 0.03 M Tris-HCl buffer (pH 7.2) containing 0.13 M NaCl.

The dialyzed TNF solution was rechromatographed on the DEAE-Sepharose CL-6B column (3.0×30 cm) equilibrated with 0.03 M Tris-HCl buffer (pH 7.2) containing 0.15 M NaCl. The adsorbed TNF was eluted with a linear NaCl gradient consisting of 500 ml of the equilibrating buffer and 500 ml of 0.03 M Tris-HCl buffer (pH 7.8) containing 0.3 M NaCl. The flow rate was 40 ml/hour, and 10-ml fractions were collected. The fractions with TNF activity were pooled and concentrated.

The concentrate was gel-filtered through the column (5×100 cm) of Sephacryl S-200 (manufactured and sold by Pharmacia) equilibrated with 5 mM phosphate buffer (pH 7.0) containing 0.15 M NaCl. The elution was performed with the equilibrating buffer. The flow rate was 80 ml/hour, and 13-ml fractions were collected. The fractions with TNF activity were pooled and concentrated by ultra-filtration.

The TNF solution thus obtained was found to have a specific activity of $5.0 \times 10^5$ U/mg-protein and have a purity 10,000-fold higher than that of the plasma.

The thus obtained TNF solution was subjected to rechromatography on the same column (Sephacryl S-200) using the same buffer, thereby to obtain a TNF solution having a specific activity of $1.0 \times 10^6$ U/mg-protein.

EXAMPLE 1

Rabbit TNF, having a specific activity of $5.0 \times 10^5$ U/mg, obtained according to the procedures as described in the Referential Example was diluted with 0.1 M phosphate buffer (pH 7.0) containing 0.15 M sodium chloride to obtain a TNF solution having a TNF activity of 1,200 U/ml. To aliquots of the thus obtained TNF solution, each of HSA (human serum albumin), BSA (bovine serum albumin), PHG-1 (partially hydrolyzed gelatin), HGG (human gamma globulin) and SPS (salmon protamine sulfate) was separately added as a stabilizing agent to form two different solutions respectively having a concentration of 0.1 mg/ml and a concentration of 1.0 mg/ml.

For each of the resulting solutions, the remaining activity was determined with respect to (i) the samples respectively subjected to storing for 2 days, 7 days and 30 days at 4° C., (ii) the samples respectively subjectd to one cycle and three cycles of freezing (−70° C.) and thawing, and (iii) the sample subjected to freezing at −70° C., lyophilization and storing for 7 days at 25° C. In carrying out the above test, the TNF solution in which no stabilizing agent was incorporated was used as control. With respect to the lyophilized preparation [see (iii) above], it was dissolved in sterile distilled water and then subjected to assay of the TNF activity.

To determine the remaining activity, the activity of each sample was assayed in vitro or in vivo, according to the methods as described hereinbefore. In the in vitro method, the remaining activity (%) was calculated from the assay value according to the following equation:

Remaining activity (%) = $A/B \times 100$ wherein A is the TNF activity of the sample after storing or physical treatment and B is the TNF activity of the sample before storing or physical treatment In the in vivo method, each sample solution was concentrated to have a concentration 20 times that at start by means of the Mini-Module NM-3 (trade mark of the ultra-filtration equipment manufactured and sold by Asahi Chemical Industry Co. Ltd., Japan). Then, 0.5 ml of each of the thus concentrated TNF solutions was injected, through the tail vein, into each of a group of five tumor-bearing mice. The TNF activity was assayed 24 hours later in accordance with the criterion as described hereinbefore. The results obtained are shown in Table 1.

EXAMPLE 2

To aliquots of the TNF solution having the same TNF activity as that employed in Example 1, each of HSA, PHG-1, HGG and SPS (these proteins are the same as those used in Example 1) was separately added as the stabilizing agent at varied concentrations. Each of the resulting solutions was stored at 4° C. for 7 days, and then subjected to the assay of the TNF activity according to the in vitro method. The remaining TNF activity (%) was calculated in the same manner as in Example 1. The results obtained are shown in FIGS. 1 to 4.

EXAMPLE 3

Rabbit TNF, having a specific activity of $1.0 \times 10^6$ U/mg, obtained according to the procedures described in the Referential Example was diluted with 0.1 M phosphate buffer (pH 7.0) containing 0.15 M sodium chloride, thereby to obtain a TNF solution having a TNF activity of 1,000 U/ml. To aliquots of the thus obtained TNF solution, two varied kinds of stabilizing agents selected from various albumins, globulins, protamines and gelatins were jointly added at varied concentrations as indicated in Table 2. Each of the resulting solutions was stored at 4° C. for 7 days, and subjected to the assay of the TNF activity according to the in vitro assay method. The remaining TNF activity (%) was calculated in the same manner as in Example 1. The results obtained are shown in Table 2.

TABLE 2

Stabilizing effect of various stabilizing agents

| Stabilizing agent (concentration, mg/ml) | Remaining TNF activity, % Storing at 4° C. for 7 days |
|---|---|
| None (Control) | 5 |
| BSA(0.05) + HSA(0.05) | 96 |
| HSA(0.01) + PHG-1(0.05) | 90 |
| HPS(0.1) + PHG-1(0.05) | 95 |
| BGG(1.0) + CEA(1.0) | 93 |

TABLE 1

Stabilizing effect of HSA, BSA, PHG-1, HGG and SPS

| Stabilizing agent | Concentration, mg/ml | Control (before storing or physical treatment) in vitro | Control (before storing or physical treatment) in vivo | Storing at 4° C. (Solution) in vitro 2 days | Storing at 4° C. (Solution) in vitro 7 days | Storing at 4° C. (Solution) in vitro 30 days | Storing at 4° C. (Solution) in vivo 7 days | Freezing-thawing in vitro repetition 1 | Freezing-thawing in vitro repetition 3 | Storing at 25° C. (lyophilized preparation) in vitro 7 days | Storing at 25° C. (lyophilized preparation) in vivo 7 days |
|---|---|---|---|---|---|---|---|---|---|---|---|
| Control (without stabilizing agent) | — | 100 | +++4, ++1 | 52 | 26 | 4 | +3, −2 | 30 | 8 | 40 | +4, −1 |
| HSA | 0.1 | 100 | +++4, ++1 | 102 | 95 | 90 | +++3, ++2 | 90 | 82 | 95 | +++3, ++2 |
|  | 1.0 | 100 | +++4, ++1 | 100 | 98 | 92 | +++4, +1 | 100 | 94 | 102 | +++4, ++1 |
| BSA | 1.0 | 100 | +++4, ++1 | 99 | 98 | 93 | +++4, +1 | 102 | 96 | 96 | +++3, ++2 |
| PHG-1 | 0.1 | 100 | +++4, ++1 | 96 | 94 | 88 | +++3, ++2 | 95 | 85 | 97 | +++4, ++1 |
|  | 1.0 | 100 | +++4, ++1 | 103 | 97 | 91 | +++4, ++1 | 101 | 93 | 100 | +++5 |
| HGG | 0.1 | 100 | +++4, ++1 | 94 | 90 | 87 | +++3, +2 | 88 | 80 | 93 | +++3, ++2 |
|  | 1.0 | 100 | +++4, ++1 | 102 | 97 | 90 | +++3, ++2 | 100 | 90 | 98 | +++3, ++2 |
| SPS | 0.1 | 100 | +++4, ++1 | 95 | 90 | 87 | +++3, ++2 | 93 | 80 | 90 | +++3, ++2 |
|  | 1.0 | 100 | +++4, ++1 | 101 | 96 | 90 | +++4, +1 | 100 | 92 | 97 | +++4, ++1 |

Note:
The figures in the columns marked "in vitro" represent the remaining activity as defined hereinbefore.
The figures in the columns marked "in vivo" represent the number of mice. The meaning of symbols (−, +, ++, etc) is given hereinbefore.
HSA: product of Sigma Chemical Co., U.S.A.
BSA: product of Armour Pharmaceutical Co., U.S.A.
PHG-1: product of Nippi Co., Ltd., Japan (High grade gelatin)
HGG: product of Nutritional Biochemicals Corp. U.S.A.
SPS: product of Sigma Chemical Co., U.S.A.

TABLE 2-continued

Stabilizing effect of various stabilizing agents

| Stabilizing agent (concentration, mg/ml) | Remaining TNF activity, % Storing at 4° C. for 7 days |
| --- | --- |
| HGG(0.1) + SPS(0.1) | 94 |

Note:
As BSA, HSA, PHG-1, HGG, and SPS, the same materials as those used in Example 1 were employed.
HPS: product of Sigma Chemical Co.
BGG: product of Sigma Chemical Co.
CEA: product of Nutritional Biochemicals Corp.

EXAMPLE 4

To aliquots of the TNF solution having the same TNF activity as that employed in Example 3, various albumins as indicated in Table 3 were separately added as the stabilizing agent in such an amount as will cause the resulting solution to have a concentration of 1.0 mg/ml. Each of the resulting solutions was stored at 4° C. for 7 days, and subjected to the assay of the TNF activity according to the in vitro assay method. The remaining activity (%) was calculated in the same manner as in Example 1. The results obtained are shown in Table 3.

TABLE 3

Stabilizing effect of various albumins

| Stabilizing agent | Remaining TNF activity, % Storing at 4° C. for 7 days |
| --- | --- |
| None (Control) | 5 |
| HSA | 98 |
| HSA fraction | 97 |
| BSA | 98 |
| BSA fraction | 98 |
| CEA | 90 |
| BLA | 91 |

Note:
As HSA, BSA and CEA, the same materials as those used in Examples 1 and 3 were employed.
HSA fraction: Human serum albumin fraction (Cohn fraction V), product of Sigma Chemical Co.
BSA fraction: Bovine serum albumin fraction (Cohn fraction V), product of Sigma Chemical Co.
BLA: product of Sigma Chemical Co.

EXAMPLE 5

To aliquots of the TNF solution having the same TNF activity as that employed in Example 3, various gelatins as indicated in Table 4 were separately added as the stabilizing agent in such an amount as will cause the resulting solution to have a concentration of 1.0 mg/ml. Each of the resulting solutions was stored at 4° C. for 7 days, and subjected to the assay of the TNF activity according to the in vitro assay method. The remaining TNF activity (%) was calculated in the same manner as in Example 1. The results obtained are shown in Table 4.

TABLE 4

Stabilizing effect of various gelatins

| Stabilizing agent | Remaining TNF activity, % Storing at 4° C. for 7 days |
| --- | --- |
| None (Control) | 4 |
| PHG-1 | 97 |
| PHG-2 | 99 |
| PHG-3 | 99 |

TABLE 4-continued

Stabilizing effect of various gelatins

| Stabilizing agent | Remaining TNF activity, % Storing at 4° C. for 7 days |
| --- | --- |
| PG | 96 |

Note:
As PHG-1, the same material as that used in Example 1 was employed.
PHG-2: product of Nippi Co., Ltd.
PHG-3: product of Sigma Chemical Co., (Gelatin Type IV: Approx. 60 Bloom)
PG: product of Nakarai Chemicals Co., Ltd., Japan

EXAMPLE 6

To aliquots of TNF solution having the same TNF activity as that employed in Example 3, various globulins as indicated in Table 5 were separated added as the stabilizing agent in such an amount as will cause the resulting solution to have a concentration of 1.0 mg/ml. Each of the resulitng solutions was stored at 4° C. for 7 days, and subjected to the assay of the TNF activity according to the in vitro assay method. The remaining TNF activity (%) was calculated in the same manner as in Example 1. The results obtained are shown in Table 5.

TABLE 5

Stabilizing effect of various globulins

| Stabilizing agent | Remaining TNF activity, % Storing at 4° C. for 7 days |
| --- | --- |
| None (Control) | 4 |
| HGG | 97 |
| BGG | 95 |
| Plasmin-treated HGG | 93 |
| Pepsin-treated HGG | 94 |
| Sulfonated HGG | 91 |
| HGG fraction | 99 |

Note:
As HGG and BGG, the same materials as those used in Examples 1 and 3 were employed.
Plasmin-treated HGG: Venoglobulin (trade mark), product of The Green Cross Corporation, Japan
Pepsin-treated HGG: Gamma-Venin (trade mark), product of Hoechst Japan Ltd.
Sulfonated HGG: Venilon (trade mark), product of Chemo-Sero-Therapeutic Research Institute, Japan
HGG fraction: Human gamma globulin fraction (Cohn fraction II), product of Sigma Chemical Co.

EXAMPLE 7

To aliquots of the TNF solution having the same TNF activity as that employed in Example 3, various protamines as indicated in Table 6 were separately added as the stabilizing agent in such an amount as will cause the resulting solution to have a concentration of 1.0 mg/ml. Each of the resulting solutions was stored at 4° C. for 7 days, and subjected to the assay of the TNF activity according to the in vitro assay method. The remaining TNF activity (%) was calculated in the same manner as in Example 1. The results obtained are shown in Table 6.

TABLE 6

Stabilizing effect of various protamines

| Stabilizing agent | Remaining TNF activity, % Storing at 4° C. for 7 days |
| --- | --- |
| None (Control) | 6 |
| SPS | 96 |
| SPF | 93 |
| SPP | 95 |

TABLE 6-continued

Stabilizing effect of various protamines

| Stabilizing agent | Remaining TNF activity, % Storing at 4° C. for 7 days |
|---|---|
| HPS | 93 |

Note:
As SPS and HPS, the same materials as those used in Examples 1 and 3 were employed.
SPF: product of Sigma Chemical Co.
SPP: product of Sigma Chemical Co.

EXAMPLE 8

Rabbit TNF, having a specific activity of $1.0 \times 10^6$ U/mg, obtained according to the procedures described in the Referential Example was diluted with 0.1 M phosphate buffer (pH 7.0) containing 0.15 M sodium chloride, whereby TNF solutions respectively having TNF activities of 100 U/ml, 1,000 U/ml, 10,000 U/ml and 100,000 U/ml were prepared. To an aliquot of each of the thus prepared TNF solutions, HSA was added in such an amount as will cause the resulting solution to have a concentration of 1.0 mg/ml. Each of the resulting TNF solutions was stored at 4° C. for 7 days, and subjected to the assay of the TNF activity according to the in vitro assay method. The remaining TNF activity (%) was calculated in the same manner as in Example 1. As control, another aliquot of each of the TNF solutions in which no HSA was incorporated was also subjected to the assay of the TNF activity. The results obtained are shown in Table 7.

TABLE 7

Stabilizing effect of HSA

| Concentration of TNF, U/ml | Concentration of HSA, mg/ml | |
|---|---|---|
| | 0 (control) | 1.0 |
| 100 | 3 | 85 |
| 1,000 | 5 | 98 |
| 10,000 | 45 | 101 |
| 100,000 | 48 | 99 |

[The figures represent the remaining activity of TNF (%).]

COMPARATIVE EXAMPLE

To aliquots of the TNF solution having the same TNF activity as that employed in Example 1, each of various amino acids, metal salts and chelating agents, which are well-known stabilizing agents for the solutions of ordinary physiologically active substances, was separately added in a varied concentration, as shown in Table 8. Each of the resulting solutions was stored at 4° C. for 7 days, and subjected to the assay of the TNF activity according to the in vitro assay method. The remaining TNF activity (%) was calculated in the same manner as in Example 1. The results obtained are shown in Table 8.

TABLE 8

Comparison of various stabilizing agents with respect to stabilizing effect

| Stabilizing agent | Concentration | Remaining TNF activity, % Storing at 4° C. for 7 days |
|---|---|---|
| None (Control) | — | 26 |
| HSA | 1.0 (mg/ml) | 98 |
| PHG-1 | 1.0 (mg/ml) | 97 |
| HGG | 1.0 (mg/ml) | 97 |
| SPS | 1.0 (mg/ml) | 90 |
| Glycine | 0.1 (M) | 30 |
| L-Lysine | 0.1 (M) | 28 |
| L-Arginine | 0.1 (M) | 24 |
| L-Glutamic acid | 0.1 (M) | 23 |
| $CaCl_2$ | 1 (mM) | 32 |
| $MgCl_2$ | 1 (mM) | 32 |
| EDTA | 1 (mM) | 26 |

Note:
As HSA, PHG-1, HGG and SPS, the same materials as those used in Example 1 were employed.

What is claimed is:

1. A method for stabilizing Tumor Necrosis Factor, which comprises adding to an aqueous solution or powder containing Tumor Necrosis Factor an effective amount of at least one stabilizing agent selected from the group consisting of an albumin, a gelatin, a globulin, a protamine and a salt of protamine.

2. A method according to claim 1, which further comprises subjecting to lyophilization the resulting aqueous solution having said stabilizing agent added thereto.

3. A method according to claim 1, wherein said stabilizing agent is added in an amount of about 10 μg to 50 mg per ml of the aqueous solution containing Tumor Necrosis Factor, said aqueous solution having a TNF activity of $10^2$ to $10^9$ units/ml.

4. A method according to claim 3, which further comprises subjecting to lyophilization the resulting aqueous solution having said stabilizing agent added thereto.

5. A method according to claim 3, wherein said stabilizing agent is added in an amount of about 100 μg to 10 mg per ml of the aqueous solution containing Tumor Necrosis Factor, said aqueous solution having a TNF activity of $10^2$ to $10^9$ units/ml.

6. A method according to claim 5, which further comprises subjecting to lyophilization the resulting aqueous solution having said stabilizing agent added thereto.

7. A method according to claim 1, wherein said stabilizing agent is an albumin.

8. A method according to claim 7, wherein said albumin is human serum albumin.

9. A method according to claim 8, wherein said human serum albumin is added in an amount of about 10 μg to 50 mg per ml of the aqueous solution containing Tumor Necrosis Factor, said aqueous solution having a TNF activity of $10^2$ to $10^9$ units/ml.

10. A method according to claim 9, which further comprises subjecting to lyophilization the resulting aqueous solution having the human serum albumin added thereto.

11. A method according to claim 9, wherein said human serum albumin is added in an amount of about 100 μg to 10 mg per ml of the aqueous solution containing Tumor Necrosis Factor, said aqueous solution having a TNF activity of $10^2$ to $10^9$ units/ml.

12. A method according to claim 11, which further comprises subjecting to lyophilization the resulting aqueous solution having the human serum albumin added thereto.

13. A method according to claim 1, wherein said stabilizing agent is a gelatin.

14. A method according to claim 13, wherein said gelatin is a water-soluble partially hydrolyzed gelatin.

15. A method according to claim 14, wherein said water-soluble partially hydrolyzed gelatin is added in an amount of about 10 μg to 50 mg per ml of the aqueous solution containing Tumor Necrosis Factor, said aqueous solution having a TNF activity of $10^2$ to $10^9$ units/ml.

16. A method according to claim 15, which further comprises subjecting to lyophilization the resulting aqueous solution having the water-soluble partially hydrolyzed gelatin added thereto.

17. A method according to claim 15, wherein said water-soluble partially hydrolyzed gelatin is added in an amount of about 100 μg to 10 mg per ml of the aqueous solution containing Tumor Necrosis Factor, said aqueous solution having a TNF activity of $10^2$ to $10^9$ units/ml.

18. A method according to claim 17, which further comprises subjecting to lyophilization the resulting aqueous solution having the water-soluble partially hydrolyzed gelatin added thereto.

19. A method according to claim 1, wherein said stabilizing agent is a globulin.

20. A method according to claim 19, wherein said globulin is human gamma globulin or a derivative thereof.

21. A method according to claim 20, wherein said human gamma globulin or derivative thereof is added in an amount of about 10 μg to 50 mg per ml of the aqueous solution containing Tumor Necrosis Factor, said aqueous solution having a TNF activity of $10^2$ to $10^9$ units/ml.

22. A method according to claim 21, which further comprises subjecting to lyophilization the resulting aqueous solution having the human gamma globulin or derivative thereof added thereto.

23. A method according to claim 21, wherein said human gamma globulin or derivative thereof is added in an amount of about 100 μg to 10 mg per ml of the aqueous solution containing Tumor Necrosis Factor, said aqueous solution having a TNF activity of $10^2$ to $10^9$ units/ml.

24. A method according to claim 23, which further comprises subjecting to lyophilization the resulting aqueous solution having the human gamma globulin or derivative thereof added thereto.

25. A method according to claim 1, wherein said stabilizing agent is a protamine or a salt of protamine.

26. A method according to claim 25, wherein said protamine or salt of protamine is added in an amount of about 10 μg to 50 mg per ml of the aqueous solution containing Tumor Necrosis Factor, said aqueous solution having a TNF activity of $10^2$ to $10^9$ units/ml.

27. A method according to claim 26, which further comprises subjecting to lyophilization the resulting aqueous solution having the protamine or salt of protamine added thereto.

28. A method according to claim 26, wherein said protamine or salt of protamine is added in an amount of about 100 μg to 10 mg per ml of the aqueous solution containing Tumor Necrosis Factor, said aqueous solution having a TNF activity of $10^2$ to $10^9$ units/ml.

29. A method according to claim 28, which further comprises subjecting to lyophilization the resulting aqueous solution having the protamine or salt of protamine added thereto.

30. A stable aqueous solution or powder which contains Tumor Necrosis Factor and an effective amount of at least one stabilizing agent selected from the group consisting of an albumin, a gelatin, a globulin, a protamine and a salt of protamine.

31. A stable aqueous solution or powder according to claim 30, wherein said stabilizing agent is contained in an amount of about 10 μg to 50 mg per ml of the aqueous solution containing Tumor Necrosis Factor, said aqueous solution having a TNF activity of $10^2$ to $10^9$ units/ml, or is contained in an amount of about 10 μg to 50 mg per ml of an aqueous solution having a TNF activity of $10^2$ to $10^9$ units/ml which solution is one obtained by dissolving the powder containing Tumor Necrosis Factor.

32. A stable aqueous solution or powder according to claim 31, wherein said stabilizing agent is contained in an amount of about 100 μg to 10 mg per ml of the aqueous solution containing Tumor Necrosis Factor, said aqueous solution having a TNF activity of $10^2$ to $10^9$ units/ml, or is contained in an amount of about 100 μg to 10 mg per ml of an aqueous solution having a TNF activity of $10^2$ to $10^9$ units/ml which solution is one obtained by dissolving the powder containing Tumor Necrosis Factor.

33. A stable aqueous solution or powder according to claim 30, wherein said stabilizing agent is an albumin.

34. A stable aqueous solution or powder according to claim 33, wherein said albumin is human serum albumin.

35. A stable aqueous solution or powder according to claim 34, wherein said human serum albumin is contained in an amount of about 10 μg to 50 mg per ml of the aqueous solution containing Tumor Necrosis Factor, said aqueous solution having a TNF activity of $10^2$ to $10^9$ units/ml, or is contained in an amount of about 10 μg to 50 mg per ml of an aqueous solution having a TNF activity of $10^2$ to $10^9$ units/ml which solution is one obtained by dissolving the powder containing Tumor Necrosis Factor.

36. A stable aqueous solution or powder according to claim 35, wherein said human serum albumin is contained in an amount of about 100 μg to 10 mg per ml of the aqueous solution containing Tumor Necrosis Factor, said aqueous solution having a TNF activity of $10^2$ to $10^9$ units/ml, or is contained in an amount of about 100 μg to 10 mg per ml of an aqueous solution having a TNF activity of $10^2$ to $10^9$ units/ml which solution is one obtained by dissolving the powder containing Tumor Necrosis Factor.

37. A stable aqueous solution or powder according to claim 30, wherein said stabilizing agent is a gelatin.

38. A stable aqueous solution or powder according to claim 37, wherein said gelatin is a water-soluble partially hydrolyzed gelatin.

39. A stable aqueous solution or powder according to claim 38, wherein said water-soluble partially hydrolyzed gelatin is contained in an amount of about 10 μg to 50 mg per ml of the aqueous solution containing Tumor Necrosis Factor, said aqueous solution having a TNF activity of $10^2$ to $10^9$ units/ml, or is contained in an amount of about 10 μg to 50 mg per ml of an aqueous solution having a TNF activity of $10^2$ to $10^9$ units/ml which solution is one obtained by dissolving the powder containing Tumor Necrosis Factor.

40. A stable aqueous solution or powder according to claim 39, wherein said water-soluble partially hydrolyzed gelatin is contained in an amount of about 100 μg to 10 mg per ml of the aqueous solution containing Tumor Necrosis Factor, said aqueous solution having a TNF activity of $10^2$ to $10^9$ units/ml, or is contained in an amount of about 100 μg to 10 mg per ml of an aqueous solution having a TNF activity of $10^2$ to $10^9$ units/ml which solution is one obtained by dissolving the powder containing Tumor Necrosis Factor.

41. A stable aqueous solution or powder according to claim 30, wherein said stabilizing agent is a globulin.

42. A stable aqueous solution or powder according to claim 41, wherein said globulin is human gamma globulin or a derivative thereof.

43. A stable aqueous solution or powder according to claim 42, wherein said human gamma globulin or derivative thereof is contained in an amount of about 10 µg to 50 mg per ml of the aqueous solution containing Tumor Necrosis Factor, said aqueous solution having a TNF activity of $10^2$ to $10^9$ units/ml, or is contained in an amount of about 10 µg to 50 mg per ml of an aqueous solution having a TNF activity of $10^2$ to $10^9$ units/ml which solution is one obtained by dissolving the powder containing Tumor Necrosis Factor.

44. A stable aqueous solution or powder according to claim 43, wherein said human gamma globulin or derivative thereof is contained in an amount of about 100 µg to 10 mg per ml of the aqueous solution containing Tumor Necrosis Factor, said aqueous solution having a TNF activity of $10^2$ to $10^9$ units/ml, or is contained in an amount of about 100 µg to 10 mg per ml of an aqueous solution having a TNF activity of $10^2$ to $10^9$ units/ml which solution is one obtained by dissolving the powder containing Tumor Necrosis Factor.

45. A stable aqueous solution or powder according to claim 30, wherein said stabilizing agent is a protamine or a salt of protamine.

46. A stable aqueous solution or powder according to claim 45, wherein said protamine or salt of protamine is contained in an amount of about 10 µg to 50 mg per ml of the aqueous solution containing Tumor Necrosis Factor, said aqueous solution having a TNF activity of $10^2$ to $10^9$ units/ml, or is contained in an amount of about 10 µg to 50 mg per ml of an aqueous solution having a TNF activity of $10^2$ to $10^9$ units/ml which solution is one obtained by dissolving the powder containing Tumor Necrosis Factor.

47. A stable aqueous solution or powder according to claim 46, wherein said protamine or salt of protamine is contained in an amount of about 100 µg to 10 mg per ml of the aqueous solution containing Tumor Necrosis Factor, said aqueous solution having a TNF activity of $10^2$ to $10^9$ units/ml, or is contained in an amount of about 100 µg to 10 mg per ml of an aqueous solution having a TNF activity of $10^2$ to $10^9$ units/ml which solution is one obtained by dissolving the powder containing Tumor Necrosis Factor.

* * * * *